United States Patent [19]

Huber

[11] 4,147,434

[45] Apr. 3, 1979

[54] METHOD AND APPARATUS FOR DETERMINING VOLATILE AND DECOMPOSABLE COMPOUNDS BY ATOMIC ABSORPTION

[75] Inventor: Bernhard Huber, Uberlingen, Fed. Rep. of Germany

[73] Assignee: Bodenseewerk Perkin-Elmer & Co., GmbH, Uberlingen, Fed. Rep. of Germany

[21] Appl. No.: 830,817

[22] Filed: Sep. 6, 1977

[30] Foreign Application Priority Data

Sep. 8, 1976 [DE] Fed. Rep. of Germany ....... 2640285

[51] Int. Cl.² ............................................. G01J 3/30
[52] U.S. Cl. ...................................... 356/312; 356/36
[58] Field of Search ................................... 356/85, 36

[56] References Cited

U.S. PATENT DOCUMENTS

| 4,035,079 | 7/1977 | Sperling | 356/85 |
|---|---|---|---|
| 4,042,303 | 8/1977 | Huber | 356/85 |

OTHER PUBLICATIONS

Chu et al., *Analytical Chemistry*, vol. 44, No. 8, Jul. 1972, pp. 1476–1479.
Church et al., *Analytical Chemistry*, vol. 46, No. 9, Aug. 1974, pp. 1352–1355.
Chau et al., *Analytical Chemistry*, vol. 47, No. 13, Nov. 1975, pp. 2279–2281.

*Primary Examiner*—F. L. Evans
*Attorney, Agent, or Firm*—Salvatore A. Giarratana; Francis L. Masselle; John D. Crane

[57] ABSTRACT

Disclosed is an apparatus and method for using same for atomic absorption determination of volatile, thermally decomposable compounds. The test sample is converted to a gaseous sample in a reaction vessel with an inert gas atmosphere. The gaseous sample in the inert gas is then introduced into a heatable measuring cell arranged in the ray path of an atomic absorption spectrometer. To further assist decomposition, the inert gas is heated prior to entering the measuring cell.

15 Claims, 8 Drawing Figures

METHOD AND APPARATUS FOR DETERMINING VOLATILE AND DECOMPOSABLE COMPOUNDS BY ATOMIC ABSORPTION

BACKGROUND OF THE INVENTION

The invention relates to a method and apparatus for using an atomic absorption spectrometer to determine the content of volatile and decomposable compounds.

In the micro-determination of arsenic according to the method of flameless atomic absorption spectroscopy, it is known to transform the arsenic as contained in the sample material into inorganic arsenic (III) compounds and to react the same in such a way that arsine containing hydrogen is formed (see the paper of R. C. Chu, G. P. Barron, P. A. W. Baumgarner in Analyt. Chem. 44, 1476; 1972). The reaction vessel on the one hand is connected to an argon source and to a heatable cell of Vycor-glass on the other hand. The arsine containing hydrogen is, then, replaced by argon and thus flows through said heated measuring cell. At the elevated temperatures of the measuring cell, the arsine decomposes and forms arsenic, the atomic absorption of which may be measured under the conditions of the prevailing temperature.

It is also known (Bulletin M-2029; Beckman Instruments GmbH) that elements like antimony, bismuth, selenium, tellurium and others may be determined in similar manner.

The aforementioned methods and the apparatus for carrying out the same employ a flow of inert gas to transfer the gas mixture including the volatile, decomposable compound into the measuring cell of the atomic absorption spectrometer. This is advantageous because of the particularly small absorption by the inert gas itself; it is, however, of disadvantage that the proportion of the substance to be measured in the flowing gas is further reduced. The danger exists, therefore, that the compound contained in the gas flow will not be completely pyrolyzed so that it is reacted and measured only in part. Since the elements to be determined are predominantly of a kind which are present only in trace amounts, an incomplete decomposition of the volatile compound will unnecessarily impair sensitivity of the measurements.

A further disadvantage of the known apparatus is that the measuring cell is made of Vycor-glass or quartz which cannot withstand the temperatures required in flameless atomic absorption spectroscopy.

Accordingly, the principal objective of the invention is to provide a method and apparatus for carrying out the same in which heat is favorably transferred to the gas flow so that the volatile compounds become completely decomposed so that the atoms of the compound are introduced into the measurement chamber of an atomic absorption spectrometer without loss.

In accordance with the invention, this objective is achieved by the thermal decomposition occurring within a conduit prior to the entry into the measuring cell. This is achieved by heating the conduit to the decomposition temperature in a region before its junction with the measuring cell. In the region of the junction of the conduit and the measuring cell, both the conduit and the cell are heated to atomization temperature.

By such a separation of thermal decomposition and atomization, both processes can be conducted each under optimum conditions. This is accomplished since the volatile compounds have sufficiently high volatility that they are transferred with the inert gas flow into the measuring cell at the high temperatures of the conduit. If the measuring cell is heated to decomposition temperatures as well, complete decomposition of the gaseous test sample is assured.

In a modification of the method according to the invention, the conduit at a point adjacent the sample introduction orifice into the cell is heated to a temperature above the decomposition temperature while the measuring cell is not heated. Once the gaseous test sample is formed, the gaseous sample is introduced via the introduction orifice into the measuring cell and the measuring cell is, then, heated to the atomization temperature.

According to this modification of the invention, thermal decomposition and spectroscopic measurement of atomic absorption are separated in space and time. The end of the conduit adjacent the measuring cell is heated to a high temperature so that the decomposition products are deposited within the unheated measuring cell. If the temperature of the end of the conduit adjacent the measuring cell is chosen high enough, no deposit will form. The measuring cell can then be heated separately to a temperature favorable for the spectroscopic measurement of atomic absorption. Such a modification is particularly useful with atomic absorption devices having a graphite tube employed as measuring cell since the graphite tube has a sample introduction orifice in its wall through which said end of the conduit may readily become introduced into the graphite tube. Thus, installation of a specific quartz cuvette and the optical adjusting operations in the atomic absorption spectrometer associated therewith is unnecessary for the investigation of sample material containing elements which form volatile and thermally decomposable compounds.

In accordance with the invention there is provided for in the apparatus for carrying out the method, the conduit adjacent its opening into the measuring cell is furnished with a heater winding for heating the contents thereof at least to the decomposition temperature of the respective gaseous test sample.

According to the invention, the conduit may also have adjacent first and second heater windings at the conduit end adjacent the opening into the measuring cell. The second heater winding is located closest to the measuring cell and the windings may be separately energized. The first winding is generally used to heat the conduit to the decomposition temperature while the second heater may be used for heating the conduit to temperatures above the decomposition temperature.

By the configuration of two separately energizable heater windings disposed along the conduit adjacent the opening into the measuring cell, the processes of deposition and the process of measurement are separated in space and time. Advantageously, the first heater winding for thermal decomposition of the gaseous test sample is positioned upstream with respect to the second heater winding which causes some of the products of thermal decomposition to become deposited in the region of the second heater winding. By also heating the measuring cell to the decomposition temperature, decomposition products are deposited there as well. When the second heater winding and the measuring cell are simultaneously heated to the atomizing temperature, the decomposition products are atomized and carried by the inert gas into the measuring cell.

Suitably the conduit will be connected in a gas tight manner but detachably to the measuring cell. The conduit may open centrally into the measuring cell and said measuring cell may be made from quartz.

In a modification of the apparatus according to the invention, a temperature resistant metering tip is introduced into the sample introduction orifice of the measuring cell. The temperature resistant metering tip which may be made of sintered corundum is heated by energizing a winding therein to a temperatures in the range of 1000° C. thereby atomizing the decomposition products in the conduit as they enter the measuring cell.

The conduit design described above is suitable for use with a graphite tube measuring cell since it may be inserted into the graphite tube. The design eliminates the need as typified by the prior art for a separate cell for the generation, decomposition and atomization of volatile, thermally decomposable compounds. Moreover, the usual arrangement of an atomic absorption spectrometer may be employed in the measurements to be presently described with just a slight widening of the customary sample introduction orifice in the wall of the graphite tube. This is advantageous because all adjusting operations connected with the introduction of another cuvette into the atomic absorption spectrometer are eliminated.

In accordance with the invention, the temperature resistant metering tip is locatable by a positioning means at either a first position where the metering tip projects through the sample introduction orifice into the interior of the measuring cell or at a second position where the metering tip is removed from the sample introduction orifice of the measuring cell.

By such positioning means, the temperature resistant metering tip can be positioned to project into the measuring cell only during the process of thermal decomposition. The metering tip may then be removed from the measuring cell after the formation of the gaseous test sample and its decomposition, said measuring cell being then available for the measurement of the atomic absorption of the decomposition products contained therein. Such an arrangement is particularly favored for carrying our the method of the invention because the decomposition products are formed immediately in the measuring cell, thus resulting in a decomposition product concentration which is high enough for accurate measurement by atomic absorption.

Advantageously, heating of the conduit, the metering tip and the measuring cell are adapted to be controlled in a preprogrammed manner by a control unit associated with the atomic absorption spectrometer. Accordingly, control of the resistant metering tip temperature, operation of the positioning means and heating of the measuring cell are adapted for preprogrammed control in such a way that said metering tip may be heated only in its first position and said measuring cell being heated only after removal of said metering tip. Thus the entire device for generating and decomposing the volatile compounds of the respectively desired element may be formed as an accessory component of a conventional atomic absorption spectrometer, the operation of said accessory component being incorporated into the controlled run of the operational program of said atomic absorption spectrometer.

Various embodiments of the invention and working results obtained therewith are illustrated and described in detail with reference to the drawings and reference numerals wherein.

Figure 1:
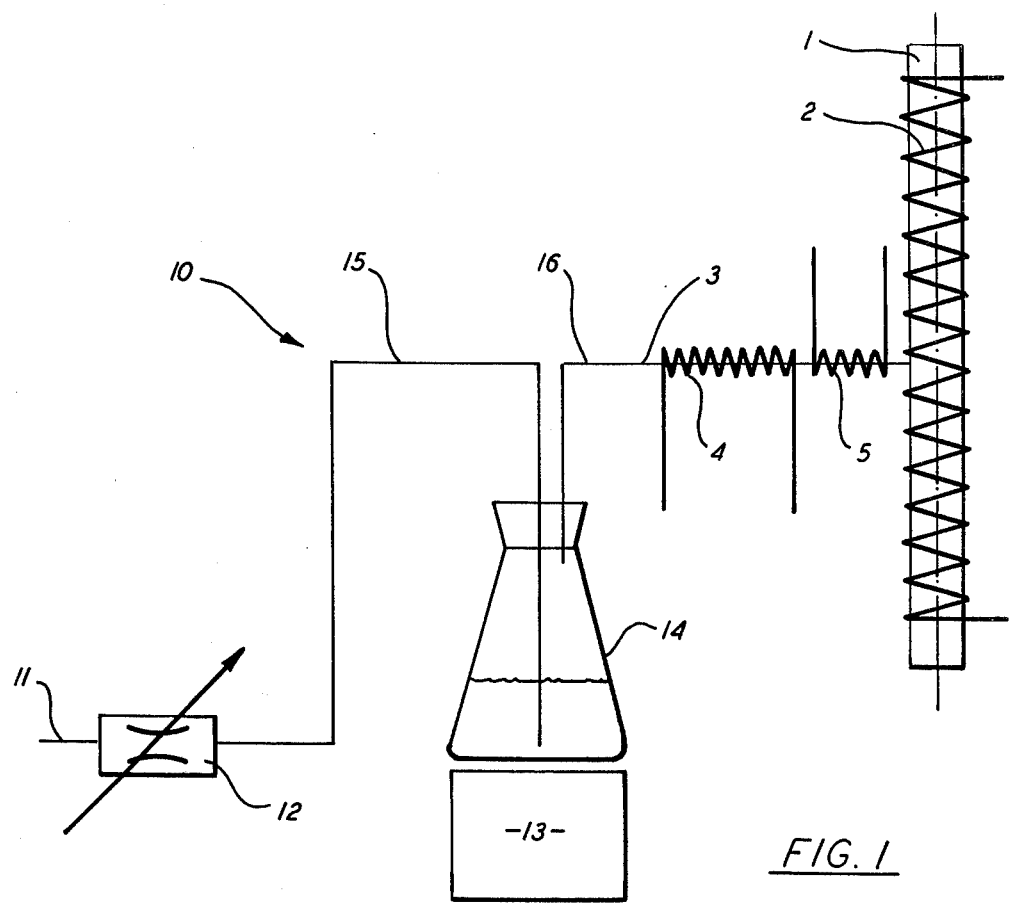
FIG. 1 is a diagrammatic representation of a first embodiment of the invention.

In FIG. 1 reference numeral 10 denotes the entire apparatus for spectroscopic determination of elements in volatile and thermally decomposable compounds. The drawing, for simplicity, does not show the atomic absorption spectrometer and equipment associated therewith for evaluation of test results. The apparatus comprises a closable reaction vessel 14 which has a conduit 15, having an adjustable flow restrictor 12 therein, which enters the vessel 14. A connection 11 is provided to an inert pressurized gas supply (not shown). A conduit 16 connects the vessel 14 with measuring cell 1. The reaction vessel 14 also has a device (not shown) for adding reagents to the prepared sample material in the inert gas atmosphere of the vessel. The desired volatile, thermally decomposable compounds are formed from the element to be determined by means of said reagents. A stirrer (not shown) within reaction vessel 14 is driven by a stirring motor 13.

Figure 2:
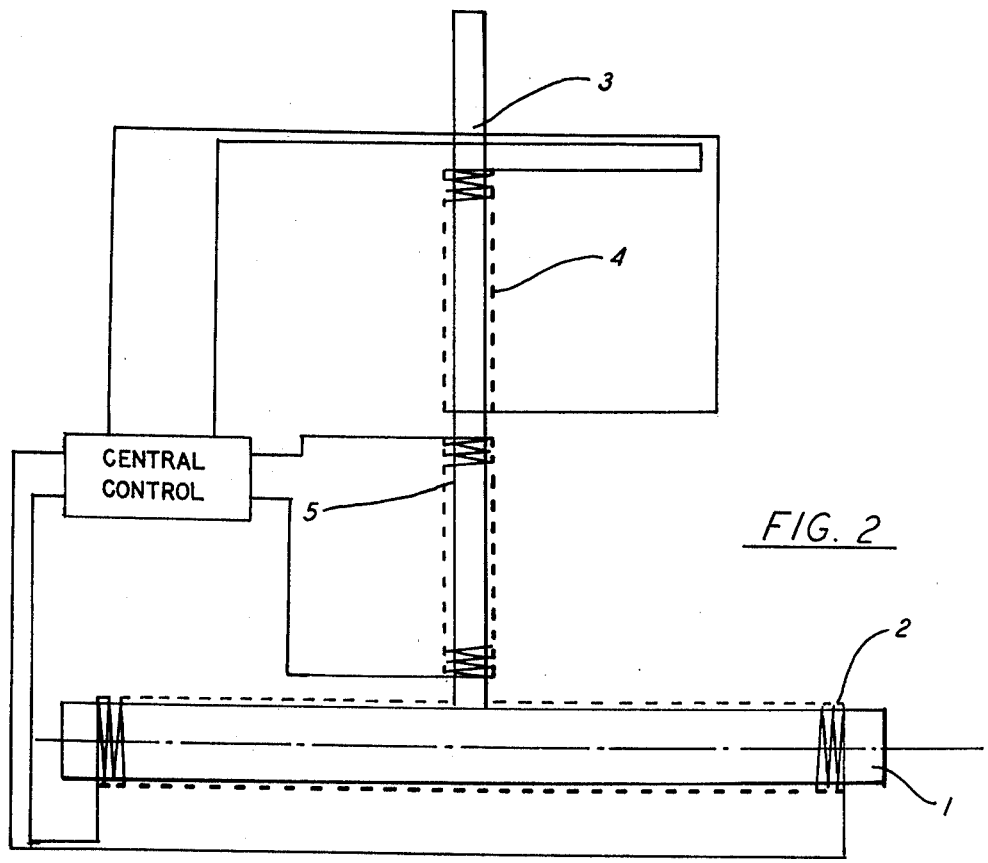
FIG. 2 is a sectional view of a portion of the embodiment as in FIG. 1 in enlarged form.

In FIG. 2, the portion 3 of conduit 16, opens into the measuring cell 1. Said portion 3 has a first heater winding 4 and a second heater winding 5, the later being located adjacent the junction with measuring cell 1. Portion 3 and the measuring cell are made, according to one embodiment of the invention, of quartz and rigidly interconnected. The measuring cell 1 has a heater winding 2.

Heater windings 2, 4 and 5 are connected to the central control unit of the atomic absorption spectrometer. The current supply to heater windings 2, 4, 5, however, need not be controlled only by the central control but may also be adjusted manually via corresponding controls.

The apparatus as represented in FIGS. 1 and 2 is operated as follows when used to determine arsenic, for example.

At first, the sample material is pretreated so that the arsenic as contained therein will be present completely in the form of inorganic compounds in the trivalent state. Such processes for sample pretreatment are known (see for instance R. C. Chu et al.) and therefore does not have to be discussed in detail here. The acidified sample solution is placed into the reaction vessel 14 and the device for reagent addition (not shown) is provided with a sufficient amount of solid sodium borohydride. The closed reaction vessel 14 is connected to an argon source via inert gas connection 11, the argon flow being adjusted by means of adjustable restrictor 12 to such a level that the entire apparatus is flushed free from air by the inert gas. The flow of argon is then reduced by means of adjustable flow restrictor 12 to a level which is satisfactory for maintaining the absence of air and for performing the analysis. Consecutively, heater windings 2 and 4 are energized to generate a decomposition temperature in the range of 500 to 1000° C. in the region of said heater windings. Afterwards, the sodium borohydride is added to the acidified sample solution causing a vigorous hydrogen evolution simultaneously with which the arsenic contained in the sample solution is transformed into arsine which is carried away by the inert gas flow. The arsine containing inert gas flow reaching the region of first heater winding 4 will assume such a high temperature that the arsine is decomposed with the arsenic liberated therefrom becoming deposited in the region of the second heater winding 5. The remaining portion of arsine is carried by the inert gas into the measuring cell 1 and arsenic becomes liberated therein because the measuring cell 1 is also heated to the decomposition temperature. After conclusion of hydride generation, the current supply to the first heater winding 4 is switched off. Then, the second heater winding 5 is energized and simultaneously the current supply to heater winding 2 is adjusted to a magnitude at which the atomization temperature is reached in the conduit 16 and the measuring cell 1. The second heater winding and the current supply thereto are selected in such a way that in the region of said heater winding temperatures of 1000° to 1200° C. are reached within portion 3 of conduit 16.

Preferably the temperature within measuring cell 1 in this measurement is about 800° C. Under such conditions the arsenic deposited in portion 3 in the region of second heater winding 5 will evaporate rapidly. Thereafter, the inert gas flow carries the arsenic into measuring cell 1 where the atomic absorption of arsenic is measured at known wavelengths.

Figure 3:
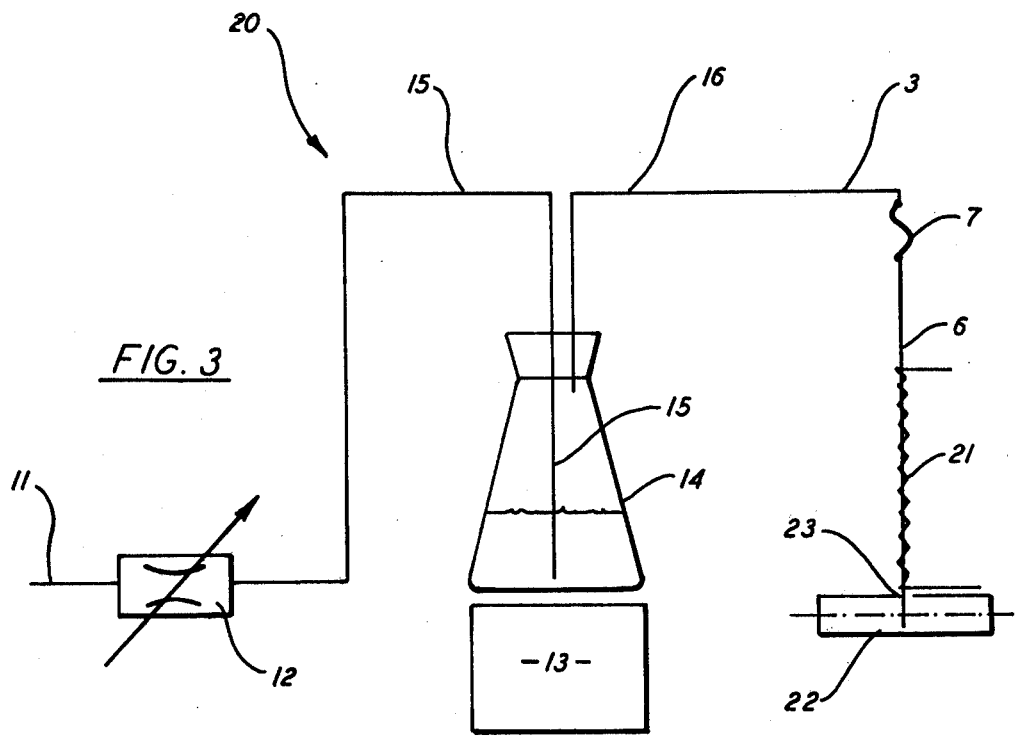
FIG. 3 is a diagrammatic view of a second embodiment of the apparatus according to the invention.

FIG. 3 shows a second embodiment of the apparatus in which figure all those members indentical with corresponding members in FIG. 1 have the same reference numerals. The apparatus denoted by reference numeral 20 comprises the reaction vessel 14 connected to an inert gas source via inert gas connection 11 and conduit 15 with a built-in flow restrictor 12. Reaction vessel 14 is provided with a device (not shown) for adding reagents to the material contained therein to generate the volatile, thermally decomposable compound from the element to be determined. Said device is designed in such a way that it may be operated within closed reaction vessel 14 without said reaction vessel being required to be opened therefor.

Figures 4, 5:
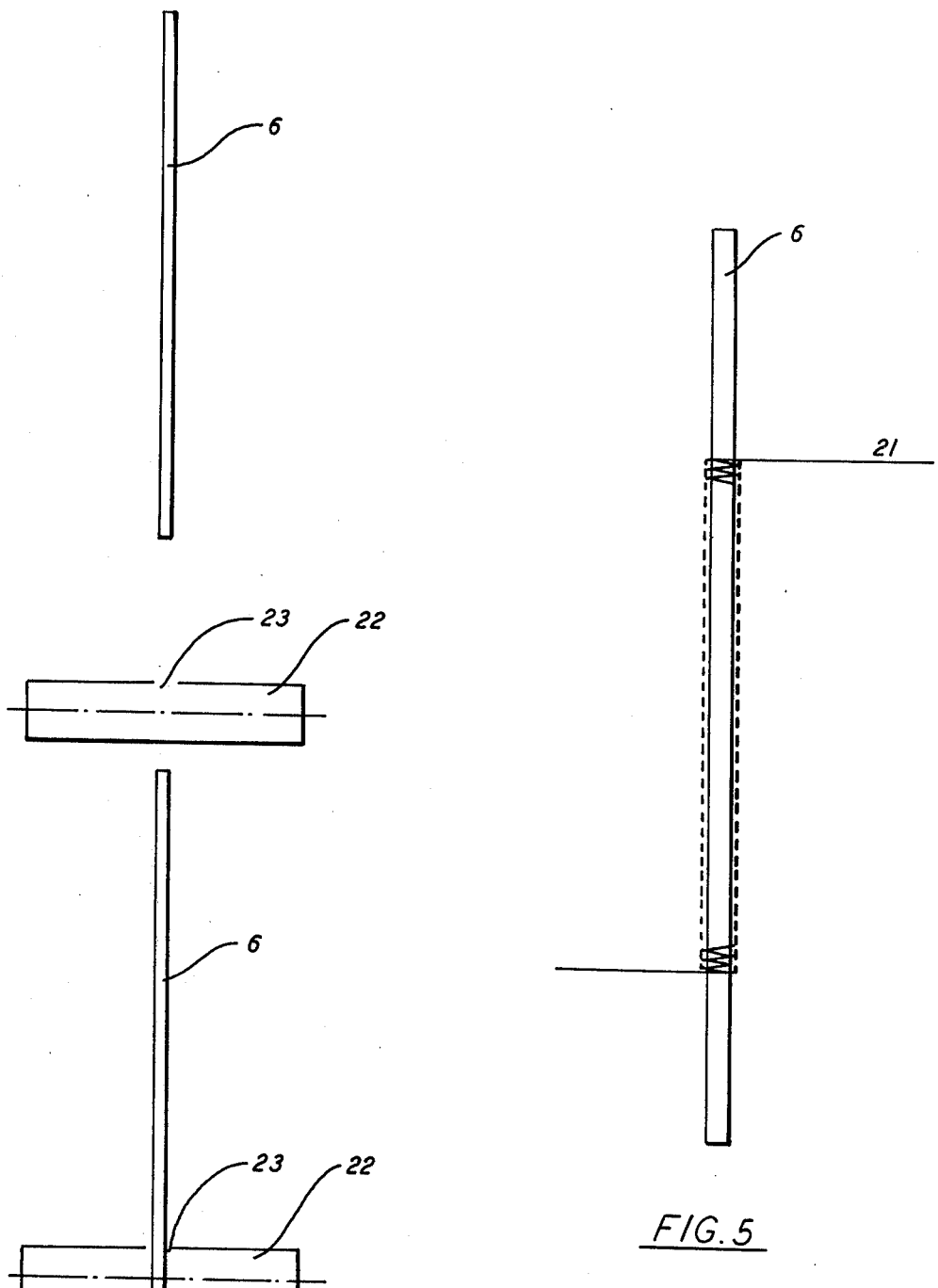
FIG. 4 is a sectional view of a portion of FIG. 3 in enlarged form.
FIG. 5 is a sectional view of a portion of FIG. 4 in enlarged form.

A conduit 16 leads from reaction vessel 14 to a graphite tube 22 of an atomic absorption spectrometer. Graphite tube 22 as indicated by the dot-dash line is positioned so the path of rays of the atomic absorption spectrometer pass therethrough. The atomic absorption spectrometer itself and its equipment for evaluation of the measuring results have been omitted also in this illustration for reasons of simplicity. Graphite tube 22 has a sample introduction orifice 23 in its wall. Portion 3 of conduit 16 carries a heater winding 21 and extends into the interior of graphite tube 22. The end portion of a metering tip 6 is made of a temperature resistant material such as sintered corundum and has an outer diameter adapted to be introduced through the sample introduction orifice 23 of graphite tube 22. The heater winding 21 is preferably made from platinum wire having a diameter of 0.02 cm with 45 windings in total (FIG. 5). Metering tip 6 is connected to conduit 16 via a flexible intermediate duct 7 preferably made from Teflon tubing.

Figure 6:
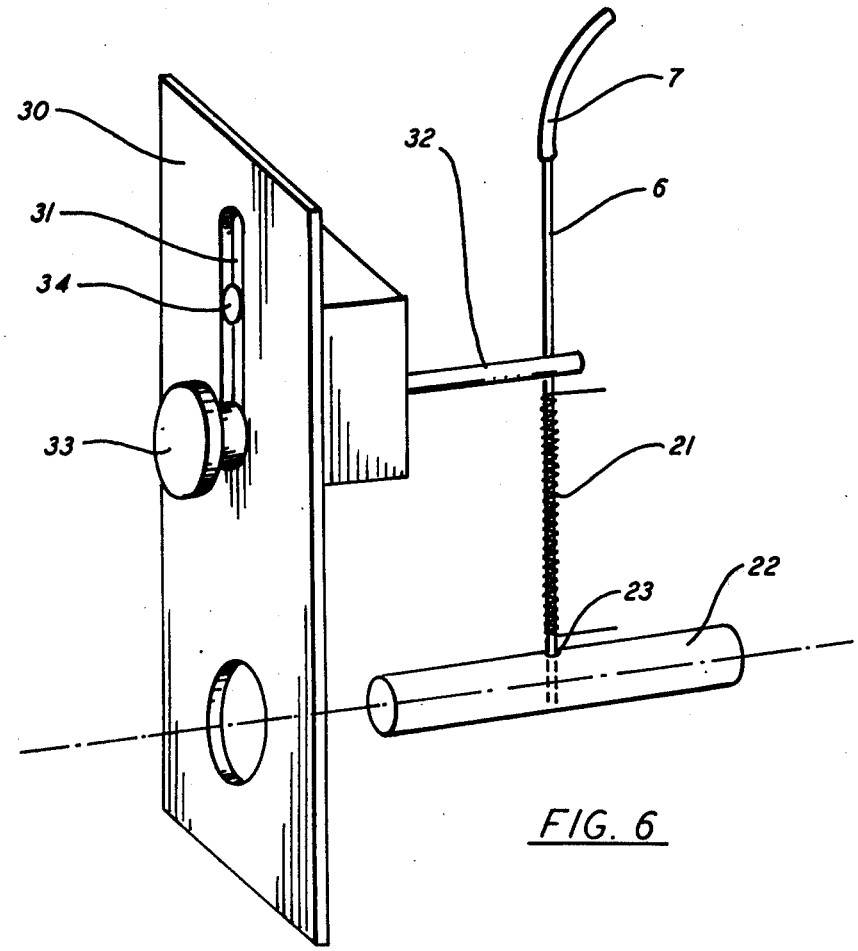
FIG. 6 is a view in detail of the positioning means for the member as shown in FIG. 4.

FIG. 6 shows a simple, manually operable means for positioning a metering tip 6 coupled by a flexible tube 7 to the conduit 16 (not shown). The positioning means comprises a support plate 30 having an elongated slot 31 with the plate 30 being secured to the atomic absorption spectrometer in any appropriate manner. A carrier 32 is guided by the elongated slot 31 and connects to the metering tip 6 at one end and carries a fastening knob 33 at its other end which projects through said elongated slot 31. By means of fastening knob 33 the carrier 32 and metering tip 6 therewith may be moved up and down the elongated slot 31. An abutment 34 which is adjustable in level if desired is provided therein to limit the upwardly directed movement of metering tip 6 while the downwardly directed movement thereof is limited by the lower end of elongated slot 31. Alternatively, there may be two adjustable limiting stops to limit upward and downward travel of the tip 6. Furthermore, the positioning means may be powered electrically, hydraulically or similarly in such a manner that its movement will occur via the central control unit of the atomic absorption spectrometer and will be correspondingly preprogrammed therein. As a further alternative, the entire conduit 16 may be readily made of flexible material so that the intermediate flexible tube 7 may be dispensed with.

For clarification, the arrangement of metering tip 6 relative to graphite tube 22 is illustrated in FIG. 4. The arrangement of metering tip 6 outside graphite tube 22 will be recognized in the upper portion thereof and in the lower portion thereof said metering tip 6 is seen as it projects through the sample introduction orifice 23 into the graphite tube 22.

The apparatus as described above is operated for the determination of arsenic as follows:

After the sample material has been prepared as described above in connection with the apparatus according to FIG. 1 and placed into reaction vessel 14, the device (not shown) for reagent addition having been supplied with sodium borohydride, the entire apparatus is at first flushed with inert gas by connecting inert gas connection 11 to an argon or other inert gas source and corresponding adjustment of flow restrictor 12. During system flushing, the metering tip 6 is at first outside the graphite tube 22 in the position as shown in the left-hand portion of FIG. 4; simultaneously the metering tip 6 is heated by the heater winding 21. After a short time period, the current supply to heater winding 21 is interrupted and metering tip 6 is introduced into graphite tube 22 by actuation of the positioning means. After a further short time interval during which also graphite tube 22 is flushed completely free of air by the argon flow, the argon flow is reduced by readjustment by the adjustable flow restrictor 12 to a level as required for the performance of the further processes. Heater winding 21 is then re-energized whereby a temperature of about 1000° C. is reached within metering tip 6. Thereafter, sodium borohydride is added to the reaction vessel 14 to form arsine containing gas which is carried in the argon flow. The arsine in the gas flow is decomposed within the heated metering tip 6 thus liberating arsenic which is deposited on the cold graphite tube 22. After conclusion of the reaction in reaction vessel 14, the metering tip 6 is removed from graphite tube 22 and the programmed analysis by the atomic absorption spectrometer is run in a known manner with the graphite tube being heated to the atomization temperature.

Figure 7:
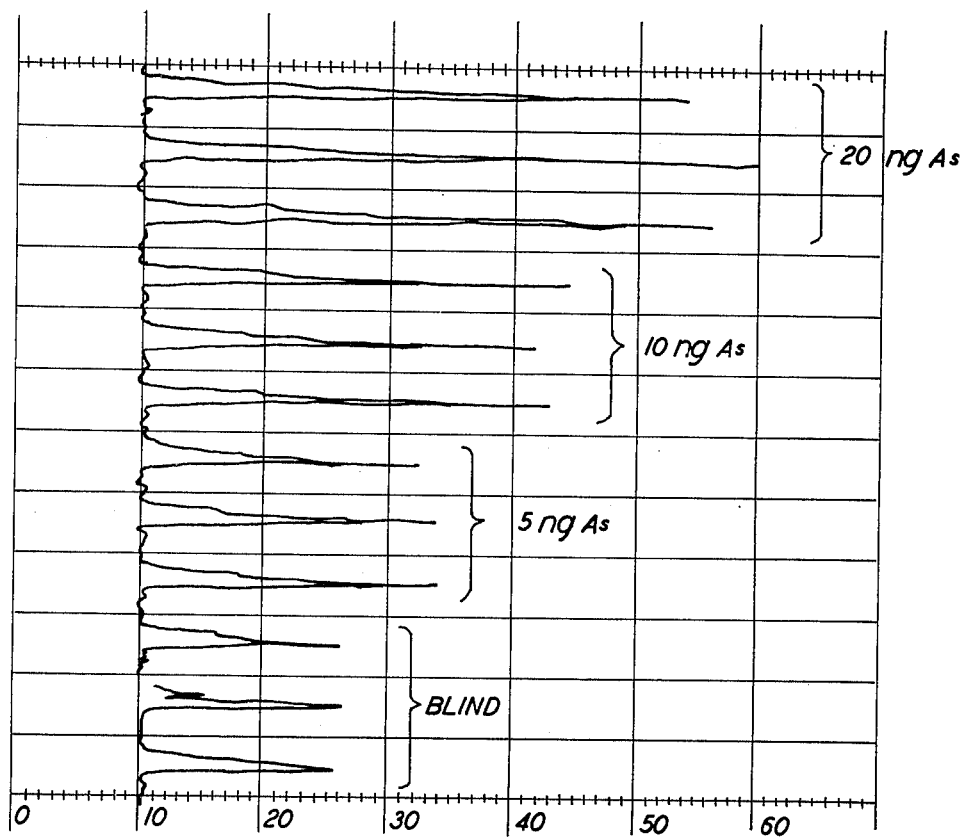
FIG. 7 is the result of a determination of arsenic by atomic absorption spectroscopy using the apparatus according to FIG. 2.

In FIG. 7, the results of an analysis obtained according to the method described above for three different samples containing different amounts of arsenic. Measurements were taken at a wavelength of 193.7 nm; the rate of argon flow during measurement amounted to 35 ml min$^{-1}$; the measuring temperature within the graphite tube cuvette was 600° C. It will be seen that despite a high blank value there is a good linear dependence of the measured signal as a function of the amount of arsenic present. The amounts of arsenic present in the respective samples were 5 and 10 and 20 ng, respectively. The measuring sensitivity is higher by at least a factor of 10 as compared to the sensitivity achieved with known apparatus as is demonstrated by a comparison of the signal levels achieved with known apparatus and with the invention.

Figure 8:
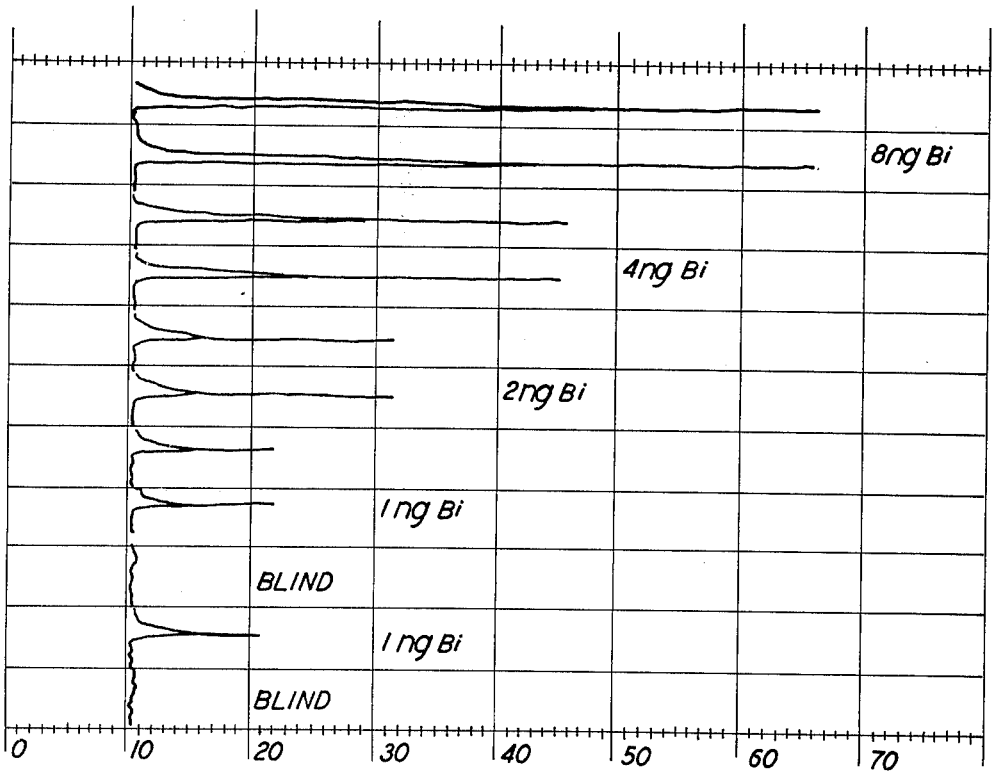
FIG. 8 is the result of a determination of bismuth by atomic absorption spectroscopy using the apparatus according to FIG. 2.

FIG. 8 illustrates a corresponding series of measurements for the determination of bismuth. The procedure is the same as for the determination of arsenic, the measuring wavelength, however, is 223 nm. Linearity in the dependence of the measured signal height on the amount of bismuth present in the sample is not as well pronounced in this case, however, the blank value is negligibly small. Reproducibility of measurement is excellent as will follow from an average deviation of 2.65 p.c. from the mean measured value. The sensitivity of measurement is extremely high; as may be derived from FIG. 8 the smallest detectable amount of bismuth present in the sample is 0.08 ng which corresponds to a proportion of 0.0032 ppb bismuth in a 25 ml sample. The measurement is thus more sensitive by orders of magnitude than measurements using known apparatus and known methods.

The method and the apparatus as described above effect considerable improvement in the microanalytical determination of such elements that form volatile and thermally decomposable hydrides. The method and apparatus according to the invention is particularly advantageous by being compatible with atomic absorption spectrometers of the type commonly found in laboratories whereby automatic operation of the apparatus is readily integrated into the program controlled operational run of said atomic absorption spectrometer. The second embodiment of the apparatus is specifically advantageous since it may be employed with the graphite tube of a commonly used atomic absorption spectrometer.

The foregoing embodiments, modifications and other modifications, which those skilled in the art to which the invention applies will readily recognize, may be made without departing from the spirit and scope of the invention which is defined by the following claims.

What is claimed is:

1. In an improved method for sample preparation in atomic absorption spectroscopic determination of elements which can form volatile, thermally decomposable compounds, the method including the steps of preparing a gaseous test sample from the sample material, transferring the gaseous test sample in an inert gas through a conduit to a heatable measuring cell and heating the measuring cell to the atomization temperature wherein the improvement comprises the step of heating the conduit to the thermal decomposition temperature to thermally decompose the gaseous test sample in the conduit prior to its entry into the measuring cell.

2. The method of claim 1 additionally including the step of heating the conduit to the atomization temperature after the conduit is heated to the thermal decomposition temperature.

3. The method of claim 1 additionally including the step of heating the measuring cell to the decomposition temperature at the same time the conduit is heated to the decomposition temperature.

4. The method of claim 1 additionally including heating the conduit at a point adjacent the measuring cell to the atomizing temperature at a time when the measuring cell is heated to the atomizing temperature.

5. The method of claim 1 additionally including the steps of inserting the conduit into the measuring cell while the conduit is heated to the decomposition temperature and withdrawing the conduit from the measuring cell prior to heating the measuring cell to the atomization temperature.

6. An apparatus for preparing a sample wherein the sample contains elements which can form thermally decomposable compounds and wherein the sample is suitable for atomic absorption determination of the elements of the sample in the apparatus comprising, in combination:
   a closable reaction vessel in which a gaseous test sample is formed;
   a source of inert gas coupled by a first conduit of said vessel to permit introduction of inert gas into said vessel;
   a measuring cell disposed to permit the rays of an atomic absorption spectrometer to pass therethrough;
   a first heating winding for heating said measuring cell to an independently selectable first temperature;
   a second conduit disposed between said measuring cell and said vessel; and
   a second heater winding for heating said second conduit in the region near the junction of said second conduit and said measuring cell, said second heater winding for heating said second conduit to at least the decomposition temperature of the test sample.

7. The apparatus of claim 6 additionally including a third heater winding disposed between said second mentioned heater winding and said measuring cell to heat said second conduit in the region of said third heater winding above the decomposition temperature.

8. The apparatus of claim 6 wherein said second conduit has a temperature resistant metering tip adapted to be inserted through a sample introduction orifice in said measuring cell.

9. The apparatus of claim 8 wherein said metering tip has a heater winding for heating said metering tip.

10. The apparatus of claim 9 wherein said metering tip is made of sintered corundum.

11. The apparatus of claim 8 wherein said metering tip is coupled to a positioning means for positioning said metering tip at either a first position whereat said metering tip is disposed within said measuring cell or a second position whereat said metering tip is disposed outside said measuring cell.

12. The apparatus of claim 11 wherein said metering tip has a heater winding which is adapted to be energized when said metering tip is at said first position.

13. The apparatus of claim 6 wherein said measuring cell is made of a graphite tube.

14. The apparatus of claim 6 wherein said heaters are adapted to be controlled by a control unit in a predetermined manner.

15. The apparatus of claim 6 wherein said first temperature is the atomization temperature.

* * * * *